(12) United States Patent
Wloka et al.

(10) Patent No.: US 8,466,320 B2
(45) Date of Patent: Jun. 18, 2013

(54) METHOD FOR THE RECOVERY OF MINERAL ACIDS FROM SALINE SOLUTIONS

(75) Inventors: Veronika Wloka, Mannheim (DE); Torsten Mattke, Freinsheim (DE); Carsten Knösche, Niederkirchen (DE); Daniel Breuninger, Bobenheim-Roxheim (DE); Nils Bottke, Mannheim (DE)

(73) Assignee: BASF SE, Ludwigshafen (DE)

( * ) Notice: Subject to any disclaimer, the term of this patent is extended or adjusted under 35 U.S.C. 154(b) by 641 days.

(21) Appl. No.: 12/602,504

(22) PCT Filed: Jun. 9, 2008

(86) PCT No.: PCT/EP2008/057170
§ 371 (c)(1),
(2), (4) Date: Dec. 1, 2009

(87) PCT Pub. No.: WO2008/152021
PCT Pub. Date: Dec. 18, 2008

(65) Prior Publication Data
US 2010/0189623 A1 Jul. 29, 2010

(30) Foreign Application Priority Data
Jun. 12, 2007 (EP) .................................. 07110073

(51) Int. Cl.
*C07C 211/00* (2006.01)
(52) U.S. Cl.
USPC .......................................... 564/330; 564/333

(58) Field of Classification Search
None
See application file for complete search history.

(56) References Cited

U.S. PATENT DOCUMENTS

| 7,408,083 B2 * | 8/2008 | Steinbrenner et al. ........ 564/331 |
| 2007/0010692 A1 | 1/2007 | Steinbrenner et al. |

FOREIGN PATENT DOCUMENTS

| DE | 101 16 316 | | 10/2002 |
| WO | 99 40059 | | 8/1999 |
| WO | 2005 007613 | | 1/2005 |
| WO | 2005007613 | * | 1/2005 |

OTHER PUBLICATIONS

"Zeolites and Other Micro- and Mesoporous Molecular Sieves" in Kirk-Othmer Encyclopedia of Chemical Technology, Jiří Čejka and David Kubička, pp. 1-30.*
"Zeolites and Other Micro- and Mesoporous Molecular Sieves" in Kirk-Othmer Encyclopedia of Chemical Technology, Jiří Čejka and David Kubička, Copyright © 2001 by John Wiley & Sons, Inc., pp. 1-30.*
"Methoden Der Organischen Chemie", Allgemeine Laboratoriumspraxis, Houben-Weyl, 4 Aufl., vol. 1, No. 1, pp. 557-558 (Jan. 1, 1958).

* cited by examiner

*Primary Examiner* — Karl J Puttlitz
(74) *Attorney, Agent, or Firm* — Oblon, Spivak, McClelland, Maier & Neustadt, L.L.P.

(57) ABSTRACT

The invention relates to a process for recovering acids from product streams of organic syntheses, which comprises the steps
a) neutralization of the acid with a base,
b) removal of the base by means of adsorption,
c) recovery of the acid.

12 Claims, No Drawings

METHOD FOR THE RECOVERY OF MINERAL ACIDS FROM SALINE SOLUTIONS

The term mineral acids is usually used in industry as a collective term for the three strong inorganic acids hydrochloric acid, nitric acid and sulfuric acid. Phosphoric acid is occasionally also included in this group of substances.

Mineral acids are obtained as by-products in many organic and inorganic processes or are used as catalysts (acid catalysts).

Hydrogen chloride is formed, for example, in large amounts in the chlorination of hydrocarbons, the synthesis of chlorofluoromethanes from tetrachloromethane, and in the phosgenation of amines to form isocyanates.

Sulfuric acid is obtained as by-product in sulfoxidations.

Hydrochloric acid is employed, for example, as homogeneous catalyst in the preparation of diphenylmethanediamine (MDA) from aniline and formaldehyde.

Sulfuric acid is, for example, used as catalyst in the synthesis of ethylene glycol from ethylene oxide or in the dehydration of diethanolamine to morpholine. A further important industrial use of sulfuric acid is the preparation of $\epsilon$-caprolactam from cyclohexanone oxime by rearrangement using sulfuric acid.

In many syntheses in which mineral acids participate, the acids are neutralized with alkalis after the reaction. For example, after the major part of the hydrogen chloride has been separated off in the abovementioned chlorofluoromethane synthesis, the remaining residues are scrubbed out in an alkali scrub.

In the synthesis of $\epsilon$-caprolactam, the lactam sulfate formed as an intermediate is converted into the free lactam by addition of ammonia with formation of ammonium sulfate.

In the synthesis of MDA, the hydrochloric acid acting as catalyst is neutralized by addition of an alkali to the reaction mixture and phase separation between an organic phase comprising the product of value and a chloride-comprising aqueous phase is thus achieved. The salt solution formed is usually disposed of. To alleviate this deficiency, WO 2005/007613, for example, has proposed omitting a neutralization and removing the acid from the reaction mixture by means of an adsorbent. However, a disadvantage here is that no phase separation occurs and the adsorbents are coated by the organic amines. This impairs the removal of the acid.

In many cases, the salt solutions obtained after neutralization or scrubbing are disposed of as wastewater. As a result, further costs for wastewater disposal are incurred in addition to the costs for acid and alkali.

It was an object of the present invention to develop a process for recovering acids and bases from neutralized aqueous solutions. The acid should be as free as possible of organic impurities, so that it can either be reused in the process or be sold as product of value.

The object has surprisingly been able to be achieved by neutralizing the acid catalyst or the acid formed in the reaction by means of a basic compound and separating the salt solution from the desired product by passing it over an acidic adsorbent.

The invention accordingly provides a process for recovering acids from product streams of organic syntheses, which comprises the steps
a) neutralization of the acid with a base,
b) removal of the base by means of adsorption,
c) recovery of the acid.

The base is retained on the adsorbent while the acid passes the adsorbent. In a regeneration step, the adsorbed base can be liberated. The acids and bases liberated in this way can either be passed to a further use or else be recirculated to the process.

The adsorbents are preferably acidic in nature and/or can form complexes with the base. Preference is given to natural or synthetic silicates, particularly preferably zeolites. The adsorbents can, if appropriate, be doped. Metal-comprising doped (with Ni, Cu, Cr or other complex formers) zeolites are also suitable for adsorption. The base is bound to the active sites while the acid passes the adsorbent.

As adsorbents, preference is given to using acid ion exchangers in the H form, with zeolites being particularly preferred.

Zeolites used are, in particular, those having a structure selected from among HEU, BEA, MOR, CHA, FAU, MFI, MEL, MWW, MTW, ZBM-11, FER, LTL, MAZ or MCM-41. The abbreviations are generally known to those skilled in the art and are published, for example, in Atlas of Zeolite Framework Types or in the Database of Zeolite Structures of the International Zeolite Association.

The zeolites employed as adsorbents are preferably used in the H form.

In an embodiment of the process of the invention, zeolites which are in the H form and are doped with metals such as nickel, chromium, copper, silver or cobalt are used as adsorbents. The amount of dopant metals is 0.5-10% by weight, preferably 1-6% by weight, based on the weight of the doped zeolites.

The adsorbents used according to the invention are preferably employed in the form of spheres, extrudates, hollow cylinders, rings, pellets or crushed material. The ratio of external surface area to volume of the shaped bodies is $>0.2$ $mm^{-1}$, preferably $>0.5$ $mm^{-1}$, particularly preferably $>1$ $mm^{-1}$. The particle volume is $<300$ $mm^3$, preferably $<100$ $mm^3$.

The adsorbents present as shaped bodies are preferably introduced in the acidic state into a fixed bed. However, they can alternatively be used in suspended form or as a moving or fluidized bed. The adsorbent can be operated in a two- or three-phase cycle of adsorption, optionally flushing and regeneration.

The flow velocities in the case of adsorption from the gas phase in a fixed bed based on the empty cross section are in the range from 0.01 to 2 m/s, preferably from 0.1 to 0.5 m/s. In the case of adsorption from a liquid phase in a fixed bed, the flow velocities based on the empty cross section are in the range from 0.01 to 10 mm/s, preferably in the range from 0.1 to 0.5 mm/s.

As described, the work-up of the aqueous salt solution is carried out by removal of the base from the neutralization of the acid by means of an adsorbent.

In the first step, the aqueous salt solution is, if appropriate after concentration, passed over the adsorbent. The adsorption phase is ended as soon as the concentration of the base in the exiting solution is $>50\%$, preferably $>10\%$, particularly preferably $>1\%$, of that in the solution which enters.

The aqueous phase can be passed through an apparatus, in particular a fixed bed, in which the adsorbent is located. It is also possible to arrange a plurality of such apparatuses in series or to connect a plurality of such apparatuses in parallel in order to be able to switch the product stream from one apparatus to another when required.

When the uptake capacity of the adsorbent present in the fixed bed has been reached, it is regenerated. Before regeneration, a flushing phase can be carried out. Here, the product remaining in the adsorbent or adsorption bed is flushed out by means of a washing liquid, in particular water.

The adsorbent is regenerated by desorption of the adsorbed component, for example by means of a temperature change, pressure change or flushing.

Regeneration is complete as soon as the loading of the adsorbent with the base corresponds to the equilibrium value of the target or outlet concentration of the base during the adsorption phase.

In the case of ammonia as neutralizing agent, the regeneration of the adsorbent can also be effected by increasing the temperature. This can be brought about either by direct heating using a heated fluid stream or else indirectly via heat transfer surfaces.

In one desorption variant, the adsorbent is dried by means of superheated gas and ammonia is driven off in this way.

When ammonia is used as neutralizing agent, adsorption can also be effected after decomposition of the ammonium salt formed. This is particularly advantageous in the case of the use of hydrochloric acid as catalyst and ammonia as neutralizing agent in step a). The aqueous solution of ammonium chloride obtained is for this purpose vaporized at a temperature above the decomposition temperature of ammonium chloride into ammonia and hydrogen chloride. The gaseous mixture is then passed over the adsorbent and the separation into ammonia and hydrogen chloride is achieved in this way. Desorption can be effected by increasing the temperature further, reducing the pressure or flushing.

The adsorption apparatus can be configured in the form of a fixed bed, a moving bed or a fluidized bed. It is also conceivable to suspend an adsorbent (stirred vessel) and subsequently separate it off, for example by means of a filter, screen or cyclone.

In a specific application, the process of the invention is utilized in the synthesis of diphenylmethanediamine. This is carried out in the following steps:

A) reaction of aniline with formaldehyde in the presence of an acid,
B) neutralization of the acid with gaseous ammonia or an ammonia-comprising solution,
C) separation of the reaction mixture from step B) into an aqueous phase and an organic phase,
D) separation of the base from the aqueous phase obtained in step C) by treatment with an acidic adsorbent.

As acid in process step A), preference is given to using a mineral acid, in particular hydrochloric acid.

The preparation of MDA in step A) is carried out, as described above, by reaction of aniline with formaldehyde in the presence of acids as catalysts. Such processes are generally known and are described, for example, in Kunststoffhandbuch, Volume 7, Polyurethane, Carl Hanser Verlag Munich, Vienna, 3rd Edition, 1993, pages 76 to 86, and in a large number of patent applications, for example WO 99/40059.

In place of or in admixture with formaldehyde, it is also possible to use at least one formaldehyde-releasing compound. In particular, the formaldehyde is used as aqueous formalin solution, alcoholic formalin solution, hemiacetal, methylenimine of a primary or secondary amine or N,N'-methylenediamine and also paraformaldehyde.

The process of the invention can be carried out continuously, semicontinuously or batchwise, preferably continuously or semicontinuously.

In a continuous process, the reactants are metered into a reactor in the desired ratio to one another and an amount of reaction product equal to the feedstream is taken from the reactor. Reactors used are, for example, tube reactors. In a continuous or semicontinuous process, the reactants are metered into a batch reactor which is preferably provided with a stirrer and/or a pumped circuit and from which the fully reacted reaction product is taken and passed to work-up.

The process of the invention is preferably carried out at a molar ratio of aniline to formaldehyde of greater than 2. The molar ratio of acid to aniline is preferably greater than 0.05. At these ratios, there is increased formation of the respective two-ring products in the reaction mixture.

The reaction is preferably carried out at a temperature in the range from 0 to 200° C., preferably from 20 to 150° C. and in particular from 40 to 120° C. It has been found that the proportion of the 2,2' and 2,4' isomers in the reaction product increases with increasing temperature.

The pressure in the reaction is 0.1-50 bar absolute, preferably 1-10 bar absolute.

When the reaction is carried out batchwise and semicontinuously, the reaction mixture can be subjected to aging after all the starting materials have been introduced. For this purpose, the reaction mixture is left in the reactor or transferred to another, preferably stirred reactor. The temperature of the reaction mixture is preferably above 75° C., in particular in the range from 110 to 150° C., during aging.

The preparation in step A) is followed by the neutralization b) of the reaction mixture. Neutralization can be carried out using the above-described bases.

In a preferred embodiment of the process, ammonia is used as base. For this purpose, ammonia is introduced in gaseous form or as an aqueous solution into the reaction mixture.

The mixture from step B) is present in the form of an organic phase and an inorganic phase. These phases are separated in step C). The phases can, for example, be separated from one another by decantation. The respective phases are then worked up.

The aqueous phase, which consists essentially of water, the salts of the acid used as catalyst dissolved therein and possibly excess base and also traces of the starting materials aniline and formaldehyde and also the end product MDA, is passed over an acidic adsorbent in step D).

The ammonia separated off in step D) is, if appropriate, worked up further, for example by removal of moisture, and can then be reused in step B).

In step D), the base is retained in the adsorbent while the acid used as catalyst passes the adsorbent. As a result, the streams leaving the adsorbent comprise the acids which have been used as catalysts in step A). These acids can, if appropriate after prior concentration, be recirculated as catalysts to step A) or be added to the acids used as catalysts.

The organic phase separated off in step C), which comprises predominantly MDA together with residues of water, the base, in particular ammonia, and the starting materials for the preparation of MDA, is likewise worked up. This is effected, for example, by washing one or more times with water or preferably by multiple distillation to separate off, for example, aniline and water.

The process of the invention enables mineral acids to be separated off and recovered in high purity from industrial processes in a simple manner.

The invention is illustrated by the following examples.

EXAMPLE 1

500 g of a crushed natural clinoptilolite (material clinoptilolite, 1-2 mm, from RS Minerals, Guisborough, Cleveland, GB) were placed in an exchanger column. To convert the zeolites into the H form, 2 l of a 25% strength aqueous $NH_4Cl$ solution were heated to 70° C. and circulated through the exchanger column by pumping for 2 hours.

The NH$_4$Cl solution was then replaced by 2 l of fresh 25% strength aqueous NH$_4$Cl solution and this was again circulated at 70° C. by pumping for 2 hours. A third exchange cycle using fresh NH$_4$Cl solution was subsequently carried out in the same way. 2 l of a 5% strength aqueous HCl solution were then pumped through the exchanger column at room temperature. Finally, the zeolite was washed with water until free of chloride, dried (10 hours at 120° C., air) and calcined at 500° C. in a stream of air for 5 hours.

426 g of the clinoptilolite in the H form having a BET surface area, determined by nitrogen adsorption, of 211 m$^2$/g were obtained. According to elemental analysis, the zeolite after the treatment has the following composition: 5.7% by weight of Al, 37% by weight of Si, 0.09% by weight of Ca, 0.14% by weight of Na, 0.38% by weight of K, 0.85% by weight of Fe, 0.21% by weight of Mg.

EXAMPLE 2

500 g of a mordenite zeolite TZM-1013 (from Tricat GmbH, 06749 Bitterfeld, D) were kneaded with 25 g of Walocel, 178.7 g of methylsilicone Silres® MSE 100 (from Wacker-Chemie, 81737 Munich, Germany) and 340 ml of water for 45 minutes and subsequently extruded at a pressing pressure of 110 bar through 2 mm dies to give extrudates. Drying was carried out at 120° C. in air for 6 hours, and the extrudates were subsequently calcined at 550° C. in a stream of air for 10 hours.

623 g of zeolite extrudates having an Al content of 3.9% by weight were obtained.

EXAMPLE 3

65 g of the mordenite zeolite from example 2 were placed in a 250 ml glass flask and admixed with a CuCl$_2$ solution comprising 7 g of CuCl$_2$ and 53.2 g of water. The mixture was slowly rotated on a rotary evaporator for 30 minutes at room temperature and subsequently dried at 60° C./35 mbar. The zeolite extrudates were then dried at 120° C. in air for 12 hours and finally calcined at 500° C. in a stream of air for 2 hours.

70.2 g of zeolite extrudates having an Al content of 3.9% by weight and a Cu content of 3.1% by weight were obtained.

EXAMPLE 4

In a stirred vessel, 644.6 g of aniline were admixed with 117.7 g of hydrochloric acid (32%) and, after cooling to below 60° C., 201.0 g of formaldehyde (49%) were slowly introduced over a period of 30 minutes. The mixture obtained in this way was transferred to a pressure vessel and stirred at 120° C. under autogenous pressure for 2 hours. After cooling to below 60° C., the mixture was admixed with 60.1 g of aqueous ammonia (30%) and 500 g of water and the phases were separated, giving 726 g of an organic phase comprising predominantly aniline and MDA and 796 g of an aqueous phase comprising predominantly NH$_4$Cl and residues of aniline. The aqueous phase comprised: 2.21 g/100 g of NH$_3$ and 4.57 g/100 g of chlorine. Before the aqueous solution was used in the adsorption, 100 g of it were diluted to an NH$_4$Cl concentration of about 0.1 mol/l by addition of 1200 g of water. The NH$_3$ content was 0.18 g/100 g and the chlorine content was 0.37 g/100 g.

EXAMPLE 5

The aqueous ammonium chloride solution (0.1 mol/l) obtained in example 4 was converted continuously into the gas phase at 300° C. and passed through a fused silica furnace which was operated at 300° C. and was charged with 50 ml (34.7 g) of adsorbent from example 1 (throughput: 0.0010 g of NH$_4$Cl/ml*h), with the output being analyzed every hour. At the beginning, an ammonia-free hydrochloric acid solution (0.1 mol/l) was obtained. Only after 17.5 hours of operation was the capacity of the adsorbent exhausted and ammonia appeared in the output. The capacity of the adsorbent was thus 0.47 mmol of NH$_3$/g.

The feed was subsequently shut off, the temperature in the furnace was increased to 500° C. and the volatile constituents formed were stripped out by means of a stream of nitrogen. After three hours, the adsorber was regenerated again and the originally bound ammonia was recovered.

EXAMPLE 6

In a manner analogous to example 5, the aqueous ammonium chloride solution (0.1 mol/l) from example 4 was passed over 50 ml (24.5 g) of the adsorbent described in example 2 at 300° C. (throughput: 0.0015 g of NH$_4$Cl/ml*h). After 7.25 hours of operation, the capacity of the adsorbent was exhausted and ammonia was present in the output. The capacity of the adsorbent was thus 0.41 mmol of NH$_3$/g.

EXAMPLE 7

In a manner analogous to example 5, the aqueous ammonium chloride solution (0.1 mol/l) from example 4 was passed over 50 ml (26.2 g) of the adsorbent described in example 3 at 300° C. (throughput: 0.0011 g of NH$_4$Cl/ml*h). After 17.0 hours of operation, the capacity of the adsorbent was exhausted and ammonia was present in the output. The capacity of the adsorbent was thus 0.67 mmol of NH$_3$/g.

The invention claimed is:

1. A process for preparing diphenylmethanediamine, comprising:
   A) reacting aniline with formaldehyde in the presence of a mineral acid,
   B) neutralizing the mineral acid with a base, wherein said base is at least one selected from the group consisting of ammonia, a primary amine, a secondary amine, and a tertiary amine,
   C) separating the organic phase and the inorganic phase,
   D) removing the base from the inorganic phase by means of adsorption, wherein an ion exchanger in the H form is used as an adsorbent,
   E) recovering the mineral acid.

2. The process according to claim 1, wherein the acid is selected from the group consisting of hydrochloric acid, sulfuric acid and nitric acid.

3. The process according to claim 1, wherein the adsorbent used in D) is a zeolite in the H form.

4. The process according to claim 1, wherein the base adsorbed in D) is removed again by means of desorption.

5. The process according to claim 3, wherein a zeolite having a structure selected from the group consisting of HEU, BEA, MOR, CHA, FAU, MFI, MEL, MWW, MTW, ZBM-11, FER, LTL, MAZ]] and MCM-41 is used as an adsorbent.

6. The process according to claim 3, wherein a zeolite which is in the H form and is doped with a metal is used as the adsorbent.

7. The process according to claim 6, wherein the dopant metal is present in an amount of 0.5-10% by weight, based on the weight of the zeolite.

8. The process according to claim 1, wherein an acid ion exchanger in the H form are used as the adsorbent.

9. The process according to claim 1, wherein the adsorbent is present as a fixed bed.

10. The process according to claim 1, wherein the adsorbent is a shaped body.

11. The process according to claim 1, wherein the adsorbent is in the form of a sphere, an extrudate, a hollow cylinder, a pellet, a ring or a crushed material.

12. The process according to claim 10, wherein the ratio of external surface area to external volume of the shaped body is $>0.2 \text{ mm}^{-1}$.

* * * * *